United States Patent [19]

Ghebre-Sellassie et al.

[11] Patent Number: 4,927,639

[45] Date of Patent: May 22, 1990

[54] MODIFIED RELEASE GEMFIBROZIL COMPOSITION

[75] Inventors: Isaac Ghebre-Sellassie, Stanhope; Robert H. Gordon, Dover; Sadath U. Khan, Mine Hill, all of N.J.

[73] Assignee: Warner-Lambert Company, Ann Arbor, Mich.

[21] Appl. No.: 305,082

[22] Filed: Feb. 2, 1989

[51] Int. Cl.⁵ .................................................. A61K 9/16
[52] U.S. Cl. ..................... 424/497; 424/468; 424/469; 424/470; 424/499; 424/501
[58] Field of Search .............. 424/497, 499, 468, 469, 424/470, 501

[56] References Cited

U.S. PATENT DOCUMENTS

| | | | |
|---|---|---|---|
| 4,132,753 | 1/1979 | Blichare et al. | 264/25 |
| 4,195,084 | 3/1980 | Ong | 424/238 |
| 4,263,272 | 4/1981 | Frigerio | 424/19 |
| 4,291,016 | 9/1981 | Nougaret | 424/35 |
| 4,533,562 | 8/1985 | Ikegami et al. | 427/3 |
| 4,661,162 | 4/1987 | Kurihara et al. | 106/169 |
| 4,716,033 | 12/1987 | Denick, Jr. | 424/48 X |
| 4,778,676 | 10/1988 | Yang et al. | 424/478 |
| 4,814,354 | 3/1989 | Ghebre-Sellassie et al. | 424/440 |
| 4,816,264 | 3/1989 | Phillips et al. | 424/468 |

FOREIGN PATENT DOCUMENTS 2554717 5/1985 France .
2179254 3/1987 United Kingdom .

*Primary Examiner*—Thurman K. Page
*Attorney, Agent, or Firm*—Mathews, Woodbridge, & Collins

[57] ABSTRACT

A disintegratable formulation of gemfibrozil providing both immediate and sustained release and comprises a tablet compressed from a mixture of a first and second granulation, and a disintegration excipient operable to effect partial or complete disintegration in the stomach. The first granulation comprises finely divided particles of pure gemfibrozil granulated with at least one cellulose derivative and the second granulation comprises finely divided particles of pure gemfibrozil granulated with a pharmaceutically acceptable water soluble or insoluble polymer which are then uniformly coated with a pharmaceutically acceptable (meth)acrylate copolymer prior to admixture with the first granulation. The first and second granulations are present in the final composition in a ratio of from about 10:1 to about 1:10.

11 Claims, No Drawings

MODIFIED RELEASE GEMFIBROZIL COMPOSITION

The present invention relates to modified release gemfibrozil formulations.

BACKGROUND

Gemfibrozil, or 5-(2,5-dimethylphenoxy)-2,2-dimethylpentanoic acid, is a widely used antihyperlipoproteinemic agent. While apparently absorbed throughout the gastrointestinal tract, maximum absorption appears to occur in the upper gastrointestinal tract and this is true notwithstanding the poor solubility of the drug at acidic pH.

Prior attempts at developing sustained release formulations, as for example reservoir systems, have not met with a great deal of success, producing either inadequate bioavailability or unacceptable release profiles. Paradoxically, it appears the achievement of a sustained release formulation requires disintegration or erosion in the stomach.

British Application No. 2,179,254 discloses compositions of analgesic propionic acid derivatives (such as ibuprofen) coated with a methacrylic-acrylic copolymer, then with a methacrylic ester copolymer, and finally with a mixture of polysorbate 80 and hydroxypropyl methylcellulose.

EPO-A No. 8600802 discloses sustained release compositions of polyethylene glycol and an amphiphilic compound.

French Application No. 2,554,717 discloses sustained release compositions which employs as the matrix a vinylpyrrolidone-vinyl acetate copolymer ans an acrylic polymer cross-linked with polyallyl sucrose. (See also Belgian application No. 901007.)

U.S. Pat. No. 4,132,753 discloses controlled release granules in which the powdered medicament is heated so as to sink into a finely divided wax material.

U.S. Pat. No. 4,195,084 discloses a liquid suspension of finely ground tall oil sitosterols for use in reducing hypercholesteraemia.

U.S. Pat. No. 4,263,272 discloses three component formulations of bile acids which release gradually or in two stages.

U.S. Pat. No. 4,291,016 discloses pharmaceutical compositions having a matrix core coated with hydroxypropyl methyl cellulose.

U.S. Pat. No. 4,533,562 discloses tablets coated with a film-forming polymer such as hydroxypropyl methylcellulose and a liquid plasticizer such as polyethylene glycol.

U.S. Pat. No. 4,661,162 discloses an enteric soluble composition containing a mixture of an entericsoluble polymer such as (m)ethyl acrylate/methacrylate copolymers and a polyanionic polymer such as alginic acid and its salts.

DETAILED DESCRIPTION

The present invention relates to a disintegratable formulation of gemfibrozil providing both immediate and sustained release. Specifically the invention comprises a tablet compressed from (i) a first granulation as hereinafter described, (ii) a second granulation as hereinafter described, and (iii) a disintegration excipient operable to effect partial or complete disintegration of the tablet in the stomach.

The first granulation comprises finely divided particles of pure gemfibrozil, or a powder blend of gemfibrozil with excipients, granulated with at least one binder such as a cellulose derivative, sugar, or polyvinyl pyrrolidone. Suitable cellulose derivatives include microcrystalline cellulose, water soluble hydroxyalkylcelluloses such as hydroxyethyl cellulose, hydroxypropyl cellulose, and hydroxypropyl methyl cellulose. Mixtures of the cellulose derivatives are particularly preferred.

The second granulation comprising finely divided particles of pure gemfibrozil, or a powder blend of gemfibrozil with excipients, granulated with a pharmaceutically acceptable water soluble or insoluble polymer with the granulation then being uniformly coated with a pharmaceutically acceptable sustaining material such as a (meth)acrylate ester copolymer and/or ethyl cellulose prior to admixture with said first granulation.

The sustaining polymeric component utilized in the second granulation contains at least one water insoluble polymer such as (meth)acrylic copolymer. The use of "meth" as a prefix in parenthesis indicates that the polymer molecule is derived from one or both of acrylic and methacrylic species. Thus, the copolymer may be derived from methyl and ethyl acrylate and methyl and ethyl methacrylate. Other conventional comonomers may be present in the copolymers as long as they do not detract from the copolymer's usefulness in the system. Particularly useful is Eudragit E30D, a polymeric dispersion of a copolymer neutral in character based on poly(meth)acrylic acid ester and having a mean molecular weight of about 800,000. Other useful polymers include cellulose derivatives having lower water solubility such as ethyl cellulose and cellulose acetate (sold as aqueous dispersions under the names Aquacoat and Surelease).

The granulations of the first and second components are carried out separately. In each case wet granulation techniques are followed, using a small amount of water and a surfactant.

The second granulation in turn is coated with a water insoluble polymer such as a (meth)acrylic copolymer of the type described above, alone or in combination with other polymers such as ethyl cellulose.

The first and second granulations are then combined in a ratio of each to the other of from about 10:1 to about 1:10, respectively. As will be seen, this ratio can be varied to produce the desired release profile. These are mixed with one or more disintegration excipients operable to effect partial or complete disintegration of the tablet in the stomach. By partial disintegration is meant the partial separation of components of the tablet or erosion of the tablet, leaving a recognizable matrix which continues to disintegrate or to otherwise release the active ingredient, gemfibrozil. Suitable disintegration and erosion excipients include one or more water dispersible cellulose derivatives such as microcrystalline cellulose, water soluble hydroxyalkylceluloses such as hydroxyethyl cellulose, hydroxypropyl cellulose, hydroxypropyl methyl cellulose, sodium croscarmelose, polyethylene glycols, sugars, and polyvinylpyrrolidone.

The combined granulations and disintegration excipients are then compressed into tablets. Processing aids such as separating agents, plasticizers, stabilizers, lubricants and the like can be added in relatively minor amounts. Useful separating or anti-tackiness agents include kaolin, talc, magnesium trisilicate, silicon dioxide, calcium carbonate and the like. Talc is preferred. Lubricants including magnesium stearate, calcium stearate, zinc stearate, colloidal silicon dioxide, stearic acid, and polyethylene glycol also assist in formulation.

Alternatively, the two granulations, formulated independently, are compressed in a two layer tablet then using a two layer press punch. Layer 1 consisting of the first granulation is first compressed and layer 2 consisting of the second granulation then is compressed over the first layer.

The tablets then are coated. The coating material is one whose solubility characteristics make it insoluble in the mouth but readily soluble in the acid environment of the gastric juices of the stomach. For handling and packaging purposes, it is preferred that the coating substance is polymeric in nature. However, other types of coating materials can be substituted for all or part of the polymeric coating.

The following examples will serve to further typify the nature of the invention but should not be construed as being a limitation on the scope thereof, which scope is defined solely by the appended claims.

EXAMPLE 1

First Granulation

A first granulation is prepared from the following components:

| Ingredient | Parts by weight |
| --- | --- |
| Gemfibrozil | 255.5 |
| Microcrystalline cellulose | 25.5 |
| Hydroxypropyl cellulose | 6.4 |
| Polysorbate 80 | 2.6 |
| Purified water | 20.0 |

The foregoing ingredients are mixed and granulated.

Second Granulation

Independently, a second granulation is prepared from the following components:

| Ingredient | Parts by weight |
| --- | --- |
| Gemfibrozil | 344.5 |
| Eudragit E30D | 137.8 |
| Polysorbate 80 | 2.8 |
| Purified water | 6.0 |

This granulation is coated with the following composition:

| Ingredient | Parts by weight |
| --- | --- |
| Eudragit E30D | 349.70 |
| Ethyl cellulose (30% aqueous dispersion) | 103.40 |

The foregoing granulations are then combined into three different formulations having compositions as follows:

| Ingredient | Parts by weight | | |
| --- | --- | --- | --- |
| | (I) | (II) | (III) |
| Granulation 1 | 290.0 | 149.9 | 60.0 |
| Granulation 2 | 524.6 | 712.4 | 833.0 |
| Microcryst. Cellulose | 219.4 | 171.7 | 141.0 |
| Croscarmellose sodium | 50.0 | 50.0 | 50.0 |

-continued

| Ingredient | Parts by weight | | |
| --- | --- | --- | --- |
| | (I) | (II) | (III) |
| Talc | 8.0 | 8.0 | 8.0 |
| Calcium stearate | 8.0 | 8.0 | 8.0 |

The three formulations above were subjected to in vitro release analysis yielding the following release profiles:

| Time (hours) | % Released Composition | | |
| --- | --- | --- | --- |
| | (I) | (II) | (III) |
| 1 | 66.0 | 50.9 | 38.5 |
| 2 | 79.1 | 68.2 | 57.8 |
| 4 | 89.6 | 85.1 | 77.1 |
| 6 | 94.6 | 90.4 | 85.7 |
| 8 | 97.2 | 95.3 | 90.9 |
| 10 | 99.1 | 98.2 | 94.3 |
| 12 | 100.0 | 100.0 | 96.7 |

What is claimed is:

1. A disintegratable formulation of gemfibrozil providing both immediate and sustained release and comprising a tablet compressed from a mixture of (i) a first granulation, (ii) a second granulation, and (iii) a disintegration excipient operable to effect partial or complete disintegration in the stomach, said first and second granulations being present in a ratio of each to the other of from about 10:1 to about 1:10, respectively, said first granulation comprising finely divided particles of pure gemfibrozil granulated with at least one cellulose derivative and said second granulation comprising finely divided particles of pure gemfibrozil granulated with a pharmaceutically acceptable water soluble or insoluble polymer, said second granulation being uniformly coated with a water insoluble material prior to admixture with said first granulation.

2. A disintegratable formulation of gemfibrozil according to claim 1 wherein said cellulose derivative of said first granulation includes at least one of microcrystalline cellulose, water soluble hydroxyalkylcelluloses, and sodium croscarmelose.

3. A disintegratable formulation of gemfibrozil according to claim 2 wherein water soluble hydroxyalkylcelluloses are hydroxyethyl cellulose, hydroxypropyl cellulose, and hydroxypropyl methyl cellulose.

4. A disintegratable formulation of gemfibrozil according to claim 1 wherein said cellulose derivative of said first granulation includes microcrystalline cellulose and hydroxypropyl cellulose.

5. A disintegratable formulation of gemfibrozil according to claim 1 wherein said pharmaceutically acceptable water soluble or insoluble polymer of said second granulation is a pharmaceutically acceptable (meth)acrylate copolymer.

6. A disintegratable formulation of gemfibrozil according to claim 5 wherein said (meth)acrylate copolymer is a copolymer derived from methyl and ethyl acrylate and methyl and ethyl methacrylate having a mean molecular weight of about 800,000.

7. A disintegratable formulation of gemfibrozil according to claim 6 wherein said second granulation is coated with a pharmaceutically acceptable (meth)-acrylate copolymer.

8. A disintegratable formulation of gemfibrozil according to claim 7 wherein said (meth)acrylate copolymer is derived from methyl and ethyl acrylate and methyl and ethyl methacrylate and has a mean molecular weight of about 800,000.

9. A disintegratable formulation of gemfibrozil according to claim 1 wherein said disintegration excipients include one or more water dispersible cellulose derivatives.

10. A disintegratable formulation of gemfibrozil according to claim 9 wherein said disintegration excipients are selected from the group consisting of microcrystalline cellulose, hydroxyethyl cellulose, hydroxypropyl cellulose, hydroxypropyl methyl cellulose, and sodium croscarmelose.

11. A disintegratable formulation of gemfibrozil according to claim 10 wherein said disintegration excipients are microcrystalline cellulose and sodium croscarmelose.

* * * * *